(12) United States Patent
Bäck

(10) Patent No.: US 10,485,708 B2
(45) Date of Patent: Nov. 26, 2019

(54) DISPOSABLE PANT-TYPE ABSORBENT ARTICLE

(71) Applicant: Essity Hygiene and Health Aktiebolag, Göteborg (SE)

(72) Inventor: Lucas Bäck, Göteborg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 16/346,700

(22) PCT Filed: Dec. 5, 2016

(86) PCT No.: PCT/SE2016/051221
§ 371 (c)(1),
(2) Date: May 1, 2019

(87) PCT Pub. No.: WO2018/106160
PCT Pub. Date: Jun. 14, 2018

(65) Prior Publication Data
US 2019/0262189 A1  Aug. 29, 2019

(51) Int. Cl.
*A61F 13/49* (2006.01)
*A61F 13/496* (2006.01)
*A61F 13/15* (2006.01)

(52) U.S. Cl.
CPC ...... *A61F 13/15699* (2013.01); *A61F 13/496* (2013.01); *A61F 13/49012* (2013.01);
(Continued)

(58) Field of Classification Search
CPC ...... A61F 2013/49026–4903; A61F 13/49012; A61F 13/496; A61F 13/15699;
(Continued)

(56) References Cited

U.S. PATENT DOCUMENTS 7,329,245 B2   2/2008  Torigoshi et al.
2003/0055389 A1*  3/2003  Sanders ............ A61F 13/15756
                                                         604/358

(Continued)

FOREIGN PATENT DOCUMENTS

EP   2283798 A1   2/2011
EP   2 671 551   12/2013
(Continued)

OTHER PUBLICATIONS

International Search Report (PCT/ISA/210) dated Jun. 28, 2017, by the Swedish Patent Office as the International Searching Authority for International Application No. PCT/SE2016/051221.
(Continued)

Primary Examiner — Susan S Su
(74) Attorney, Agent, or Firm — Buchanan Ingersoll & Rooney P.C.

(57) ABSTRACT

A disposable pant-type absorbent article comprises an absorbent insert, wherein a region of the front or back section is made of a laminated elastic web material. A first adhesive material for securing sheets of web material of the laminated web material to each other is applied to a location adjacent an opposite lateral side of the front or back section, while leaving a first gap in the central area of the absorbent article free from the first adhesive. A second adhesive material for securing the elastic threads to the sheets of laminated web material is applied in the region from a location adjacent a first lateral side of the front or back section to a location adjacent an opposite lateral side of the front or back section, while leaving a second gap in the central area of the absorbent article free from the second adhesive material.

19 Claims, 5 Drawing Sheets

(52) U.S. Cl.
CPC .................. *A61F 2013/1591* (2013.01); *A61F 2013/15406* (2013.01)

(58) Field of Classification Search
CPC ...... A61F 13/49011; A61F 2013/49025; A61F 2013/49036
See application file for complete search history.

(56) References Cited

U.S. PATENT DOCUMENTS

| | | | |
|---|---|---|---|
| 2003/0089447 A1 | 5/2003 | Molee et al. | |
| 2003/0109842 A1* | 6/2003 | Louis ................ | A61F 13/15699 604/385.29 |
| 2006/0130964 A1 | 6/2006 | Mccabe | |
| 2011/0066127 A1* | 3/2011 | Kuwano ........... | A61F 13/49001 604/385.3 |
| 2011/0071488 A1* | 3/2011 | Kuwano ........... | A61F 13/49001 604/385.3 |
| 2012/0095429 A1* | 4/2012 | Kobayashi ........ | A61F 13/15804 604/385.16 |
| 2013/0255864 A1 | 10/2013 | Schneider et al. | |
| 2013/0255865 A1 | 10/2013 | Brown et al. | |
| 2015/0173957 A1 | 6/2015 | Schneider et al. | |
| 2018/0170027 A1* | 6/2018 | Schneider ......... | A61F 13/15585 |

FOREIGN PATENT DOCUMENTS

| | | |
|---|---|---|
| WO | 2013148381 A1 | 10/2013 |
| WO | 2015191904 A1 | 12/2015 |

OTHER PUBLICATIONS

Written Opinion (PCT/ISA/237) dated Jun. 28, 2017, by the Swedish Patent Office as the International Searching Authority for International Application No. PCT/SE2016/051221.

* cited by examiner

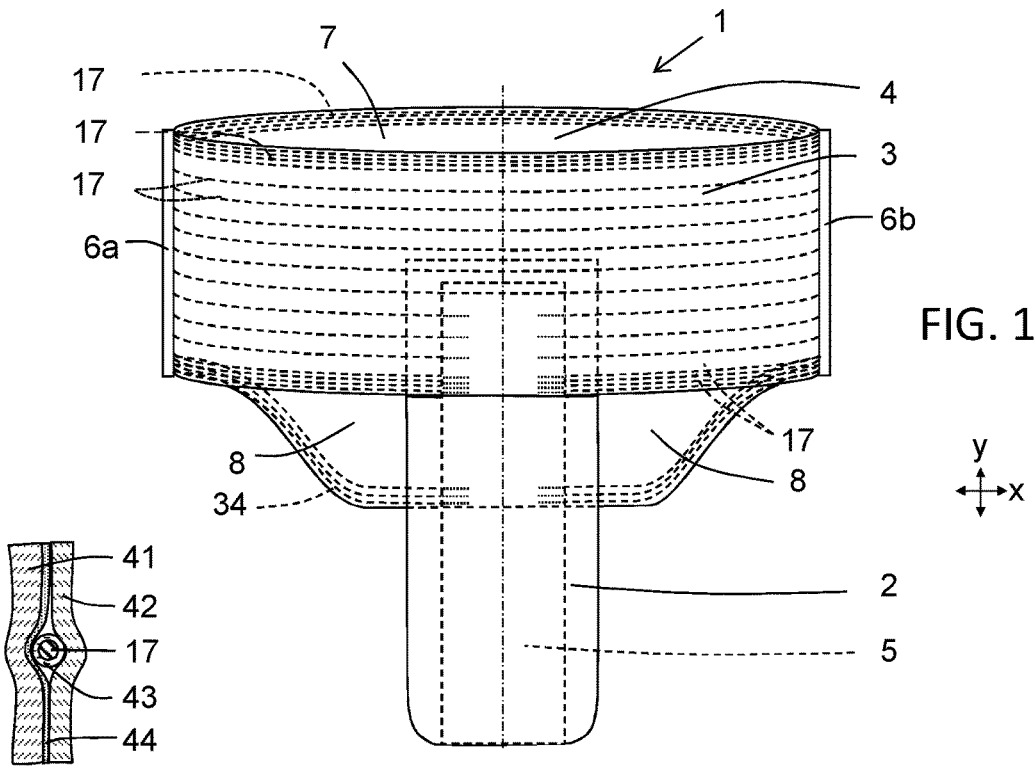
FIG. 1
FIG. 3
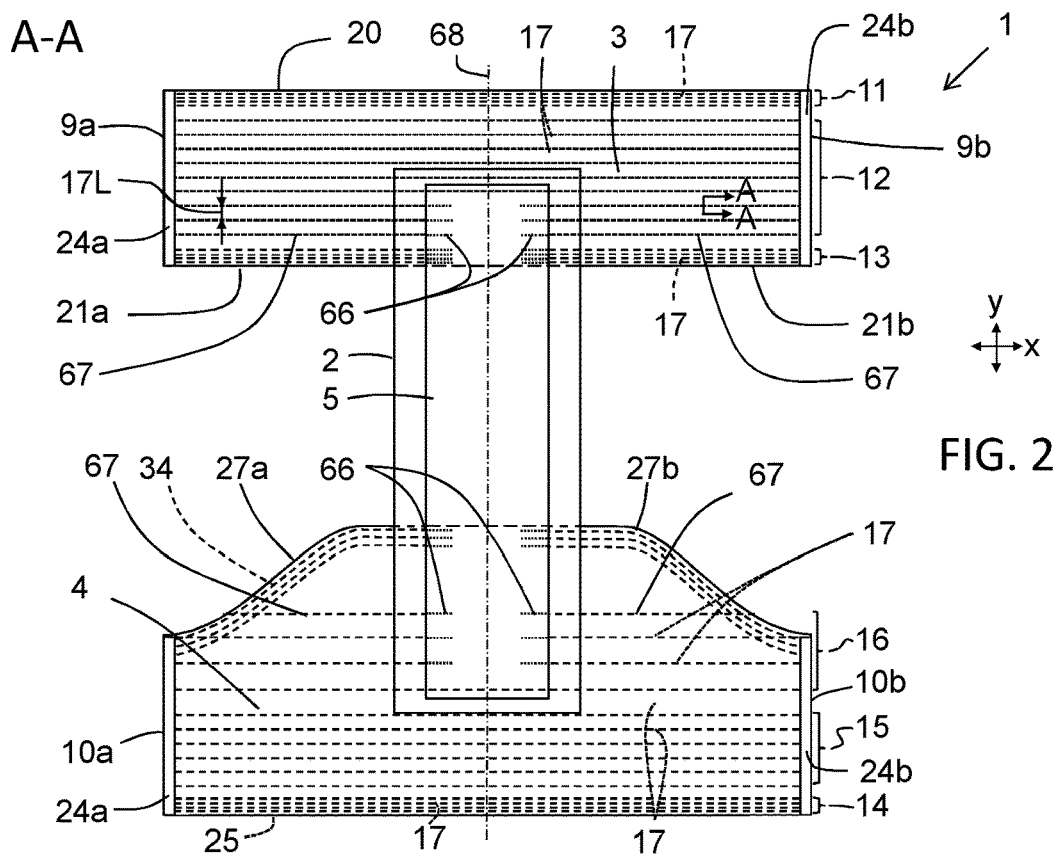
FIG. 2

DISPOSABLE PANT-TYPE ABSORBENT ARTICLE

TECHNICAL FIELD

This disclosure relates to a disposable pant-type absorbent article such as a pant diaper, a sanitary pant or incontinence pant. The disposable pant-type absorbent article comprises a chassis made of laminated web material and having a front section and a back section and an absorbent insert located mainly in a crotch portion of the article and connected to the front and back sections and having an absorbent core. A region of the front and/or back section is made of a laminated elastic web material comprising a plurality of elastic threads extending from a location adjacent a first lateral side of the front and/or back section to a location adjacent an opposite lateral side of the front and/or back section, wherein said elastic threads are interrupted in a central area of the absorbent article. The disclosure also relates to a method for manufacturing such a disposable pant-type absorbent article. The disposable pant-type absorbent article is configured for being used by males and females, babies, children or adults and may be provided in various sizes.

BACKGROUND

There is general desire in the field of disposable pant-type absorbent articles to provide absorbent articles with increased comfort and fit and that provides the user with confidence with respect to its leakage protection. Document WO 2013/148381 A1 discloses a diaper pant having a front region with deactivated elasticity and reduced adhesive strength for improved comfort and aesthetical appearance. While the known disposable absorbent garment is satisfactory for its intended use, such a disposable absorbent garment is nonetheless susceptible to improvement, in particular in terms of improved manufacturing.

SUMMARY

An object of the present disclosure is to provide a disposable pant-type absorbent article which enables improved manufacturing while keeping the advantages of controlled retraction of cut thread ends in a deactivated front and/or back central area. This object is at least partly achieved by the features of the independent claims.

The disclosure concerns a disposable pant-type absorbent article such as a pant diaper, a sanitary pant or incontinence pant, having a longitudinal direction and a transverse direction. The disposable pant-type absorbent article comprises a chassis made of laminated web material and having a front section and a back section, and an absorbent insert located mainly in a crotch portion of the article and connected to the front and back sections and having an absorbent core. A region of the front and/or back section is made of a laminated elastic web material comprising a plurality of elastic threads extending from a location adjacent a first lateral side of the front and/or back section to a location adjacent an opposite lateral side of the front and/or back section, wherein the elastic threads are interrupted in a central area of the absorbent article. A first adhesive material primarily for securing sheets of web material of the laminated web material to each other is applied in the region from a location adjacent a first lateral side of the front and/or back section to a location adjacent an opposite lateral side of the front and/or back section, while leaving a first gap in a central area of the absorbent article free from the first adhesive material. A second adhesive material primarily for securing the elastic threads to the sheets of laminated web material is applied in the region from a location adjacent a first lateral side of the region to a location adjacent an opposite lateral side of the region, while leaving a second gap in a central area of the absorbent article free from the second adhesive material. A width of the first gap in the transverse direction is smaller than a width of the second gap in the transverse direction, such that an adhesive gradient is provided in the region as seen from a centre of the absorbent article towards the lateral edges of the absorbent article.

The disclosure further concerns a method for manufacturing a disposable pant-type absorbent article such as a pant diaper, a sanitary pant or incontinence pant, having a longitudinal direction and a transverse direction), in a continuous process. The method comprises:

forming a chassis from a laminated web material and having a front section and a back section, wherein a region of the front and/or back section is made of a laminated elastic web material comprising a plurality of elastic threads extending from a location adjacent a first lateral side of the front and/or back section to a location adjacent an opposite lateral side of the front and/or back section, wherein a first adhesive material primarily for securing sheets of web material of the laminated web material to each other is applied in the region from a location adjacent a first lateral side of the front and/or back section to a location adjacent an opposite lateral side of the front and/or back section, while leaving a first gap in a central area of the absorbent article free from the first adhesive material, wherein a second adhesive material primarily for securing the elastic threads to the sheets of laminated web material is applied in the region from a location adjacent a first lateral side of the region to a location adjacent an opposite lateral side of the region, while leaving a second gap in a central area of the absorbent article free from the second adhesive material, wherein a width of the first gap in the transverse direction is smaller than a width of the second gap in the transverse direction, such that an adhesive gradient is provided in the region as seen from a centre of the absorbent article towards the lateral edges of the absorbent article, locating an absorbent insert having an absorbent core mainly in a crotch portion of the article and connecting the absorbent insert to the front and back sections, cutting said elastic threads within the area of first gap, and attaching side edges of the front section to side edges of the back section along side seams.

By leaving a second gap in the central area of the absorbent article free from the second adhesive material, i.e. the adhesive material primarily for securing the elastic threads to the sheets of laminated web material, the interrupted elastic threads will be substantially deactivated within the second gap, thereby avoiding a gathering effect of the laminated web material of the chassis in the second gap. Consequently, the second gap will provide a so called flat front and/or flat back design in which the part of the absorbent core located in the second gap will not suffer from potentially detrimental compression due to the elastic threads of the chassis.

Moreover, by applying the first adhesive material for securing sheets of web material of the laminated web material to each other within the second gap while keeping a strip of material free from the first adhesive material, improved manufacturing in combination with high comfort and fit of the absorbent article may be obtained.

By having the first adhesive material applied in the second gap a more controlled retraction of the interrupted elastic thread ends is accomplished. This has the advantage of reducing the risk that the elastic threads delaminates from the laminated web material in the region where second adhesive material is applied due to the force of the snap back of the elastic threads during the interrupting operation of the elastic threads. Moreover, the controlled retraction of the interrupted elastic threads within the second gap enables improved visual appearance because the likelihood that the deactivated ends of the elastic threads remain parallel with the still active portion of the elastic is increased. Also, the first adhesive material in the second gap reduces the risk for a significant pocket-effect in central area due to large-area lack of bonding between the sheets of web material forming the laminated web material of the front and back sections of the chassis.

Moreover, by leaving a first gap in a central area of the absorbent article free from the first adhesive material, the risk that the interrupting tool of the manufacturing equipment becomes soiled with adhesive material is reduced, thereby improving the manufacturing process. If the entire second gap is coated with the first adhesive material the interrupting tool becomes soiled and increased maintenance effort is required.

The first and second adhesive material may be of identical or different type. For example, the first and second adhesive material may be hot-melt adhesive. The first and second adhesive material is primarily distinguished from each other in terms of adhesive strength, which may be varied by varying the applied coating weight per square meter [g/m2].

The width of the first gap may be in the range of 1-7 centimetres, specifically 1.5-5.0 centimetres. Small width of the first gap requires high manufacturing precision because the first adhesive material, which is applied intermittently along the transverse direction of the absorbent article, must be applied such that the gap is formed in the centre of the absorbent article where the interrupting tool will engage and severe the elastic threads. However, too large first gap is also undesirable because this may result in increased pocket effect due to the lack of large-area bonding between the sheets of web material of the chassis, which potentially can result in a user detecting that portions of for example the belly area is made of a laminated material that appears to be poorly attached.

The width of the first gap may be in the range of 5-50%, specifically 15-40%, of the average width of the core in the region.

The width of the second gap may be in the range of 8-18 centimetres, specifically 10-15 centimetres. This width corresponds to the flat front and/or flat back area, i.e. the area where the elastic threads are deactivated due to lack of adhesive material for securing the elastic threads to the sheets of web material of the chassis.

The width of the second gap may be in the range of 130-70%, specifically 120-80%, or more specifically substantially equal with the average width of the core in the region.

The area of the first gap may be free from adhesive material. As discussed above, this is beneficial for avoiding smearing of adhesive material on the interrupting tool.

The area of the second gap excluding the area of the first gap may have an adhesive coating weight of 0.1-7 g/m2, specifically 1-4 g/m2, of the first adhesive material. The first adhesive material in the second gap is merely intended for keeping the sheets of web material of the chassis secured to each other, while being too weak for keeping the elastic threads in a tensioned state after cutting of the elastic threads in the central area.

Since no second adhesive material is applied in the second gap, only first adhesive material is applied in the second gap. Therefore the first adhesive material will have adhesive coating weight of 0.1-7 g/m2, specifically 1-4 g/m2.

The areas on lateral sides of the region outside the second gap where the first and second adhesive materials overlap may have an adhesive coating weight of 1.5-20 g/m2, specifically 2-15 g/m2. These areas will comprise both the first and the second adhesive material, and an adhesive coating weight of 1.5-20 g/m2, specifically 2-15 g/m2, is suitable for both keeping the sheets of web material of the chassis in a secured to each other, and keeping the elastic threads in a tensioned state upon cutting the elastic threads in the central area.

The second adhesive material may be applied with an adhesive coating weight of 2-15 g/m2, specifically 3-12 g/m2. This amount enables sufficient strong bonding for keeping elastic threads secured to sheets of laminated web material of the chassis.

The second adhesive material may be applied with a larger adhesive coating weight per square metre than the first adhesive material. The is a result of the higher bonding force required for securing the elastic threads to the sheets of web material of the chassis, compared with the relatively low bonding force required for keeping the sheets of web material of the chassis secured to each other.

The first adhesive material may be applied on at least one sheet of web material of the laminated web material. The first adhesive material may alternatively be applied to both sheets of web material of the laminated web material.

The first adhesive material may be applied in form of a single coating covering substantially all area within the region except for the area of the first gap, or in form of a plurality of spaced apart, substantially parallel, strips extending in the transverse direction except for the area of the first gap. With increased adhesive area a more underwear-like visual appearance is accomplished due to the reduced delamination effect otherwise caused by areas lacking first adhesive material. However, a plurality of strips of adhesive material may in certain circumstances be an acceptable compromise between underwear-like visual appearance and cost for adhesive material.

The second adhesive material may be applied on the elastic threads of the region prior to being included into the laminated elastic web material. This approach ensures that only the second adhesive material is applied to the correct location, i.e. the location of the elastic thread, as well as ensuring that the elastic thread is adhesively connected to both sheet of web material surrounding the elastic thread.

The second adhesive material may alternatively be applied on at least one sheet of web material of the laminated web material. This approach may be necessary for example when the elastic threads have a curved over the front and/or back section because a thread guidance machinery may be incompatible with applying adhesive material on the elastic threads.

The second adhesive material may be applied on at least one sheet of web material of the laminated web material along the course of those elastic threads having an orientation diverging from the transverse direction. As mentioned above, elastic threads having a course diverging from a straight line parallel with the machine direction generally requires some type of thread guidance machinery that may be incompatible with applying adhesive material on the elastic threads.

Each of the first and second gaps may extend over a plurality of elastic threads. There may thus be a plurality of elastic threads that interrupted in the front and/or back section.

The first and/or the second gap may have a substantially rectangular shape. This means that application of first and second adhesive material, respectively, is stopped and subsequently started again simultaneously over the width of the absorbent article, as seen in a machine direction, thereby enabling use of a single adhesive applicator tool for each of the first and second adhesive material, and for each of the front and/or back section.

Snapped-back elastic portions of the elastic threads within the second gap may be held in straight and parallel configuration by means of the first adhesive material. Thereby a more aesthetical and perceived well-engineered absorbent article is accomplished.

Further advantages and advantageous features of the invention are disclosed in the following description.

BRIEF DESCRIPTION OF THE DRAWINGS

With reference to the appended drawings, below follows a more detailed description of embodiments of the invention cited as examples.

In the drawings:

FIG. 1 shows a front view of an embodiment of a ready to use absorbent article, and FIG. 2 shows the absorbent article of FIG. 1 in a disassembled flat state;

FIG. 3 shows the section according to cut A-A of FIG. 2;

DETAILED DESCRIPTION OF EXEMPLARY EMBODIMENTS OF THE INVENTION

Figure 4:
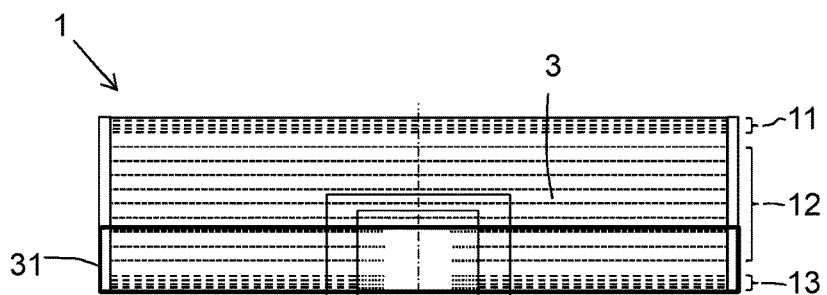
FIG. 4 shows the product of FIGS. 2 and 3, but with the regions having interrupted threads in the front and back sections 3, 4 marked with bold lines.
Figure 4:
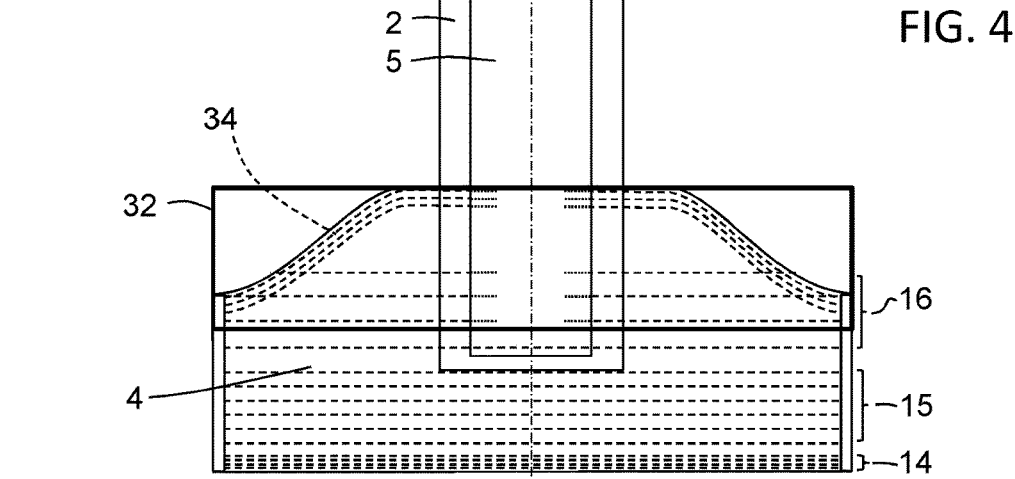

Various aspects of the disclosure will hereinafter be described in conjunction with the appended drawings to illustrate and not to limit the disclosure, wherein like designations denote like elements, and variations of the described aspects are not restricted to the specifically shown embodiments, but are applicable on other variations of the disclosure.

In FIG. 1 of the drawings an exemplary embodiment of a disposable pant-type absorbent article 1 is schematically illustrated in an assembled and ready-to-use state. The pant-type absorbent article 1 is for example pant diaper, a sanitary pant or an incontinence pant adapted for use of a male or female user. The pant-type absorbent article 1 according to the exemplary embodiment of FIG. 1 comprises a dual-piece chassis having a front section 3, a back section 4 and an absorbent insert 2 located mainly in a crotch portion of the absorbent article 1 and connected to interior side of the front and back sections 3, 4 for bridging the gap between the front and back sections 3, 4. The absorbent insert 2 comprises an absorbent core 5 for absorbing body fluid.

In short, manufacturing of the pant-type absorbent article is performed by first manufacturing two parallel continuous strips of laminated elastic web material that should form the front and back sections 3, 4 of the finished absorbent article 1.

Manufacturing of each of the laminated elastic web material of the front and back sections 3, 4 are typically performed by feeding a first and a second continuous substantially non-elastic sheet of web material, such as for example a substantially non-elastic nonwoven material, along a machine direction, which correspond to the transverse direction X in the drawings, while simultaneously feeding a plurality of continuous elastic threads 17 arranged parallel with one another. A first adhesive material is applied to any or both of the sheets of web material making up the laminated web material of the first and second sections. A second adhesive material is applied to the elastic threads, and/or applied to one or both of the sheets of web material making up the laminated web material of the first and second sections. Subsequently, the first and second sheets of web material are joined and bonded to each other with a plurality of continuous elastic threads located between the first and second sheets.

The elastic threads 17 are attached to the first and second sheets in a tensioned state. Elastic threads 17 that are attached to first and second sheets in parallel with the first and second sheets, i.e. in parallel with the machine direction or in the transverse direction X, may for example have adhesive material applied to the threads themselves before being fastened in a tensioned state to the web material. Alternatively, the web material itself may have adhesive material applied to it for securing the elastic threads 17 thereto. The latter is particularly advantageous when the elastic threads 17 exhibit a curved and/or inclined orientation over the transverse length of the finished absorbent article 1. The finished laminated elastic web will consequently gather when allowing the elastic threads 17 to return to their natural state.

However, while still keeping the elastic threads 17 in tensioned state the method further comprises a step of placing a finished absorbent insert 2 in the gap between the two parallel continuous strips of laminated elastic web, such that the absorbent insert 2 partly overlaps with the both said parallel continuous strips, and subsequently securing the absorbent insert 2 to said strips. The absorbent insert 2 is thus manufactured separately from the front and back sections 3, 4 and subsequently placed and fastened to said sections 3, 4 in a suitable manufacturing step.

The manufacturing method further includes the step of providing a flat front and/or flat back design. This involves having the elastic threads 17 free of the second adhesive material in a central area of the front and/or back section 3, 4 and performing an interrupting operating of the elastic threads 17 located in the central portion of the front and/or back section 3, 4, such that the portion of the elastic threads 17 located the central portion of the front and/or back section 3, 4 and are free from adhesive material are allowed to return to their natural, un-tensioned, state without exerting a gathering effect on the surrounding web material, thereby creating a flat area at a desired region of the front and/or back section 3, 4. A flat area is typically desirable in the area where the absorbent core 5 overlaps the front and/or back sections 3, 4 because the gathering effect of active elastic threads 17 may be deemed having a negative effect on the absorption capacity of the absorbent core 5.

After securing the absorbent insert 2 to the two parallel continuous strips of laminated elastic web the entire continuous material band is folded at a fold line extending substantially in the transverse direction X of the absorbent insert 2, such that the two parallel continuous strips of laminated elastic web becomes superposed after folding. Thereafter the two parallel continuous strips of laminated elastic web are joined to each other at discrete locations at predetermined fixed intervals along the material band using for example ultrasonic welding, to form side seams 6a, 6b of the finished absorbent article 1. Consequently, side edges 9a, 9b of the front section 3 are permanently attached to opposite side edges 10a, 10b of the back section 4 to form side seams 6a, 6b of the finished and assembled absorbent article 1, thereby also defining a waist-opening 7 and a pair of leg-openings 8.

In a final step the continuous material band is cut in a machine cross direction in the area of, or adjacent to, the side seams 6a, 6b to transform the folded continuous material band into individual absorbent articles 1. When the laminated elastic web material of the front and back sections 3, 4 is no longer held in stretched state in the transverse direction X the sandwiched stretched elastic threads 17 will cause the web material to gather, i.e. to contract in the transverse direction X and to form small undulations in the laminated elastic web material. An example manufacturing process for such an elastic web material is described more in detail in document WO2014098683 A1, which is referred to in its entirety.

In FIG. 2 of the drawings the same exemplary embodiment of the disposable pant-type absorbent article 1 is schematically illustrated in flat, non-assembled state, and without opposite side edges 9a, 9b, 10a, 10b of the front and back sections 3, 4 attached to each other. This may for example be realised by breaking the side seams 6a, 6b of a finished absorbent article 1 and unfolding the pant-type absorbent article 1 into a flat state. The pant-type absorbent article 1 comprises, in a unfolded and flat state, a longitudinal direction Y that is substantially parallel with a direction of elongation of the absorbent insert 2. The transverse direction X is perpendicular to the longitudinal direction Y.

The pant-type absorbent article 1 of the exemplary embodiment illustrated in FIG. 1 and FIG. 2 comprises a front section 3 having a waist edge 20, a pair of leg edges 21a, 21b and a pair of side edges 9a, 9b. The front section 3 has a substantially rectangular shape.

The pant-type absorbent article 1 of the exemplary embodiment illustrated in FIG. 1 and FIG. 2 further comprises a back section 4 having waist edge 25, a pair of leg edges 27a, 27b and a pair of side edges 10a, 10b.

Both the front and back section 3, 4 comprises a plurality of elastic threads 17 extending substantially parallel with the transverse direction X, but they may alternatively locally exhibit a small inclination with respect to the transverse direction X, for example if the front and/or back section 3, 4 has shape different from a rectangle.

In the exemplary embodiment of FIG. 1 and FIG. 2, the front section 3 has a waist elastic area 11 comprising a plurality of elastic threads 17, a belly elastics area 12 comprising a plurality of elastic threads 17 and a leg elastics area 13 comprising a plurality of elastic threads 17. Moreover, back section 4 has a waist elastic area 14 comprising a plurality of elastic threads 17, a back elastics area 15 comprising a plurality of elastic threads 17, buttocks elastics area 16 comprising a plurality of elastic threads 17 and a leg elastics 34 comprising a plurality of elastic threads 17.

A schematic view of a cross-section A-A of the laminated elastic web material of the front section 3 of FIG. 2 is shown in FIG. 3 comprising a first sheet 41 of web material attached to a second sheet 42 of web material by means of a first adhesive material 44. The first adhesive material 44 is here applied on the first sheet 41 of web material prior to lamination of the laminated elastic web. Moreover, an elastic thread 17 is shown sandwiched between the first and second sheets 41, 42 of web material and coated with a second adhesive material 43. Please note that the dimensions in this schematic illustration are not drawn to scale.

Since it may be advantageous to have the side seams 6a, 6b free from adhesive material the continuous elastic threads 17 will in the area of the side seam 6a, 6b during manufacturing of the absorbent article snap back upon the cutting operation required for splitting the continuous material band into individual absorbent articles. Therefore narrow longitudinal strips 24a, 24b of surface on the front and back sections 3, 4 is illustrated in FIG. 2 having no elastic threads 17 attached thereto.

The pant type absorbent article 1 according to the disclosure is provided with a so called flat-front design and/or flat-back design. This expression herein refers to a design of the absorbent article 1 where at least a portion of the elastic threads 17 extending in a substantially transverse direction X over the front and/or back section 3, 4 are interrupted in a central area of the front and/or back section 3, 4, as illustrated in FIG. 2. The elastic threads 17 within the central area of the absorbent article area may lack sufficient adhesive bonding for enabling the interrupted elastic threads 17 to gather the sheets of web material making up the front and/or back portion 3, 4 when the elastic threads 17 are interrupted in said central area. Instead, upon interrupting the elastic threads 17 within a central area, for example by cutting or severing the threads 17, the elastic threads 17 within the central area will snap back to a natural, un-stretched, state. The snapped-back un-stretched elastic portion 66 of the threads 17 are thus substantially deactivated and will not have any gathering effect on the laminated web material, while the remaining portion 67 of the elastic thread 17, where sufficient amount of adhesive material is provided to enable the elastic thread 17 to exert a gathering effect, will remain connected to the sheets of web material.

An elastic region having one or more elastic threads 17 that have been interrupted in a central portion is consequently referred to herein as being partly elastic, because said elastic region is still elastic in a major portion thereof, i.e. at the side portions of said regions outside of the central portion 65.

The cutting or breaking of the elastic threads 17 along for example a longitudinal centre line 68 of the absorbent article 1 may for example be performed with a suitable machine during the manufacturing of the absorbent article. The removal of the gathering effect otherwise caused by the elastic threads 17 in the central area results in a more smooth and flat appearance of the central area of the absorbent article 1, which is desirable for avoiding unnecessary compression of the absorbent core 5, as well as providing the user with a more cloth-like undergarment appearance and the associated sense of comfort. Obviously, the absorbent article may be provided with a flat-front design, a flat-back design, or both a flat-front and flat-back design.

FIG. 4 corresponds to the flat absorbent article of FIG. 2 but with the regions 31, 32 of the front and back section 3, 4 respectively having interrupted elastic threads 17 in a central area of the absorbent article being marked with bold lines.

In the exemplary embodiment disclosed in FIG. 4 the region 31 of the front section 3 includes elastic threads 17 of the leg elastics area 13, as well as elastic threads 17 of the belly elastics area 12. Moreover, in the exemplary embodiment disclosed in FIG. 4 the region 32 of the back section 4 includes elastic threads 17 of the buttocks elastics area 16 and elastic threads 17 of the leg elastics 34.

As mentioned above, the laminated elastic web material of the front and back sections 3, 4 is each made of at least two sheets 41, 42 of substantially non-elastic web material, such as for example a substantially non-elastic nonwoven material, and with a plurality of elastic threads 17 sandwiched between the two sheets 41, 42 of web material and arranged parallel with one another in a transverse direction of the absorbent article. A first adhesive material 44 is applied to the sheets 41, 42 of web material making up the laminated web material of the first and second sections 3, 4 for the purpose of holding said sheets 41, 42 of web material together. Without the first adhesive material 44 the sheets 41, 42 of web material would form one or pockets in the laminated elastic web material and locally delaminate. Hence, for providing perceived high quality absorbent article material with high level of underwear-like visual appearance the first adhesive material 44 is applied over large areas of the laminated elastic web material of the front and back sections 3, 4.

The first adhesive material 44 may also be referred to as constructional adhesive or light bond adhesive because it is used for constructing the laminated elastic web material and because relatively low bonding strength is sufficient for securing the sheets 41, 42 of web material of the laminated elastic web material together, especially in view of the relatively large available surface area, such that the desired high quality feeling of the absorbent article may be accomplished.

The first adhesive material 44 may be applied in a variety of ways to the sheets 41, 42 of web material. For example, the first adhesive material 44 may be applied to any of the sheets 41, 42 of web material, or both sheets 41 42 of web material. Moreover, the first adhesive material 44 may be applied as a continuous coating over a large surface of the front and/or back section 3, 4. Alternatively, the first adhesive material 44 may be applied as spaced apart parallel elongated strips (not shown) of adhesive material 44 extending in the transverse direction X for the purpose of reducing the amount of required adhesive material and thereby reducing cost.

Figure 5:
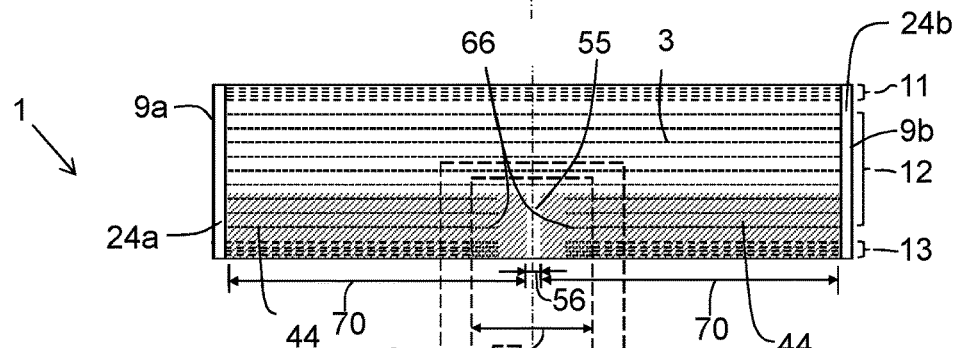
FIG. 5 shows the coating of the first adhesive material.
Figure 5:
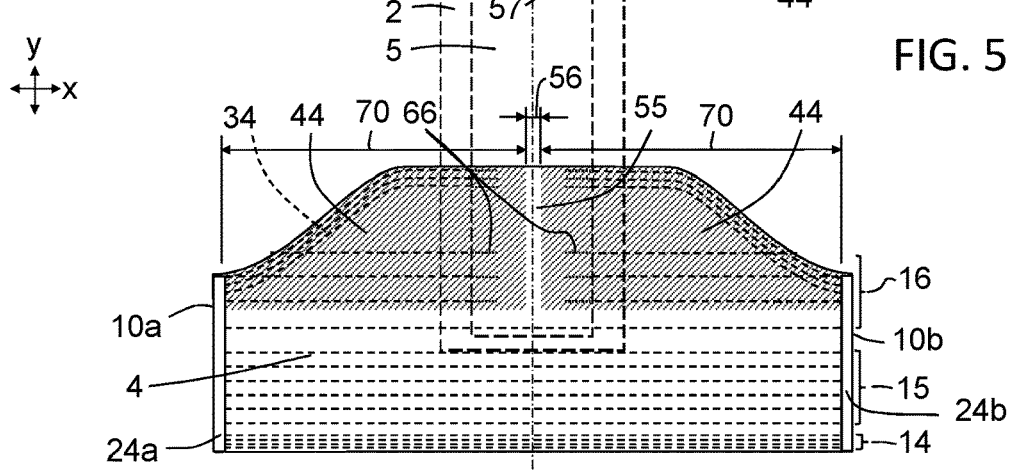

FIG. 5 illustrates schematically the flat absorbent article 1 of FIG. 2 having first adhesive material 44 applied thereto in the area marked with hatching in the front and back sections 3, 4. The first adhesive material 44 may be applied in the region 31, 32 from a location adjacent a first lateral side of the front and/or back section to a location adjacent an opposite lateral side of the front and/or back section 3, 4 for ensuring sufficient bonding between the sheets 41, 42 of web material.

The lateral sides of the front section are formed of the side edges 9a, 9b of the front section 3. The lateral sides of the back section 4 are formed of the side edges 10a, 10b of the back section 4, as well as the leg edges 27a, 27b of the back section 4.

The first adhesive material 44 may at least partly be applied continuously from a location adjacent a first lateral side of the front and/or back section 3, 4 to a location adjacent an opposite lateral side of front and/or back section 3, 4 because this enables a relatively non-complex manufacturing of the absorbent article 1. The transverse direction X corresponds to the machine direction during manufacturing of the absorbent article 1 and increased intermittent application of the first adhesive material 44 increases the speed with which the adhesive applicator tool of the manufacturing equipment must be switch between on and off, thereby increasing complexity.

The first adhesive material 44 is applied on lateral sides of the central area of the region 31, 32 while leaving a first gap 55 in a central area of the absorbent article 1 free from the first adhesive material 44.

The width 56 of the first gap 55, as measured in the transverse direction X, is in the range of 1-7 centimetres, specifically 1.5-5.0 centimetres. The width is selected large enough for allowing certain variations in position of both the first gap 55 but also the position of the interrupting tool used for interrupting the elastic threads 17 in the central area. The aim is to ensure that the interrupting tool, such as a cutting or severing tool, used for interrupting the elastic threads 17 is applied in an area lacking the first adhesive material, because the interrupting tool may otherwise be soiled with the first adhesive material, thereby requiring increased maintenance.

In other words, the width 56 of the first gap 55 of the first and/or back section 3, 4 is in the range of 5-50%, specifically 15-40%, of the average width 57 of the core 5 in the region 31, 32 of the first and/or back section, respectively.

Still in other word, the width 56 of the first gap 55 of the first and/or back section 3, 4 is in the range of 3-25%, specifically 5-20%, of the maximal length 70 of each side portion of first adhesive material 44 applied to the first and/or back section 3, 4, respectively.

According to one exemplary embodiment the area of the first gap 55 is entirely free from adhesive material, i.e. not only the first adhesive material 44, but all kinds of adhesive material.

The first adhesive material 44 may be applied with an adhesive coating weight of 0.1-7 g/m2, specifically 1-4 g/m2. This amount of first adhesive material 44 is generally sufficient for providing a sufficient bonding strength between the sheets 41, 42 of web material of the front and/or back section 3, 4.

In the exemplary embodiment shown is FIG. 5 the entire buttocks-covering portion of the back section 4 is coated with the first adhesive material and provided with an elongated first gap 55 extending in the longitudinal direction Y.

Figure 6:
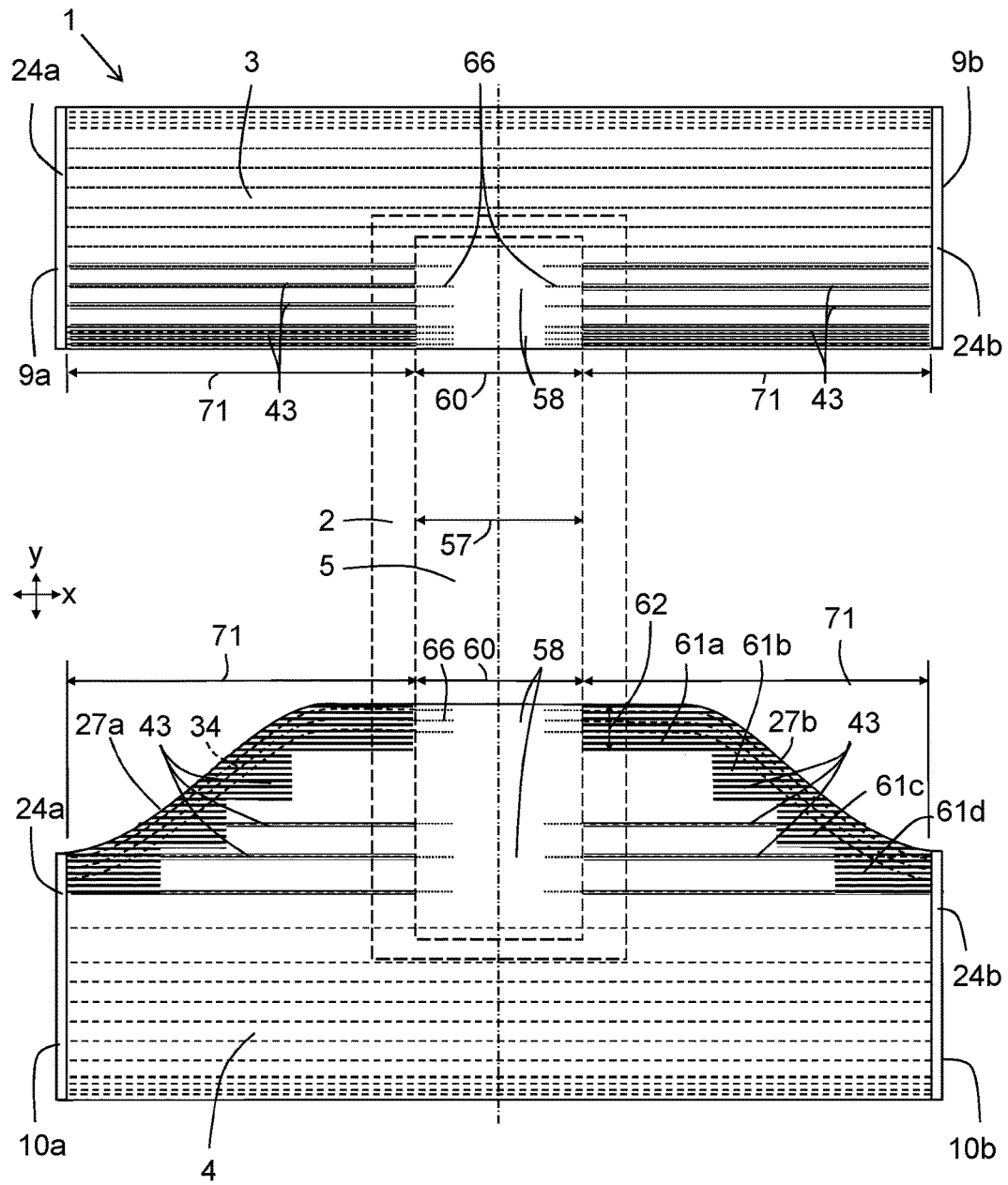
FIG. 6 shows the coating of the second adhesive material.

FIG. 6 illustrates schematically the flat absorbent article of FIG. 2 where only the second adhesive material 43 has been applied in the area marked with transverse hatching in the front and back sections 3, 4. The second adhesive material 43 is applied to the elastic threads 17, and/or applied to any or both of the sheets 41, 42 of web material making up the laminated web material of the first and second sections 3, 4. The second adhesive material 43 is primarily intended for securing the elastic threads 17 to the sheets 41, 42 of laminated web material.

If the second adhesive material 43 is applied to the elastic threads 17 before sandwiching the elastic threads 17 between the sheets 41, 42 of web material it is ensured the second adhesive material 43 is correctly placed on the sheets 41, 42 of the web material, and that the elastic thread 17 are bonded to both sheets 41, 42 of web material and not only a single sheet thereof.

However, as an alternative, the second adhesive material 43 may be applied to one or both of the sheets 41, 42 of web material. This approach may be necessary or advantageous in designs where the elastic thread 17 is not aligned with the machine direction, i.e. the transverse direction X, because then an elastic thread guidance tool may be required for guiding the elastic threads 17 to the desired curved shape over the width of the absorbent article 1, and an elastic thread guidance tool may be incompatible with adhesive coated threads 17.

If both straight and curved elastic threads 17 should be secured to the front and/or back section 3, 4 the second adhesive material 43 may be applied to one or both sheets 41, 42 of web material in the area associated with the curved elastic threads 17, and the second adhesive material 43 may additionally be applied on the straight elastic threads 17 before laminating the first and second sheets 41, 42 of web material.

If the second adhesive material 43 is applied to one or both of the sheets 41, 42 of web material the application of the first and second adhesive materials 44, 43 are preferably applied using separate adhesive applicator tools, because the first and second adhesive materials 44, 43 may be applied with different amount per square meter and with different lengths over the first and/or second sections 3, 4. The first and second adhesive material 44, 43 can be applied to the same sheet 41, 42 of web material or to different sheets 41, 42 of web material.

The second adhesive material 43 may be referred to as elastics adhesive or heavy bond adhesive because it is used for securing the elastic threads 17 in a stretched state to the flat un-stretched sheets 41, 42 of web material of the laminated elastic web material. This bonding must thus withstand relatively large forces and the surface area of the elastic thread 17 is relatively small, thereby making a reliable and strong adhesive connection difficult. Consequently, the second adhesive material 43 is typically applied with a larger adhesive coating weight per square metre than the first adhesive material 44.

The second adhesive material 43 is applied in the region from a location adjacent a first lateral side of the front and/or back section 3, 4 to a location adjacent an opposite lateral side of the front and/or back section 3, 4, while leaving a second gap 58 in a central area of the absorbent article 1 free from the second adhesive material 43. The second adhesive material 43 consequently stretches over a length 71 on each side of the second gap 58. The length 71 of the second adhesive material coating may according to exemplary embodiment be larger than the length 60 of the second gap 58, as seen in the transverse direction X.

Both the first and second adhesive materials 43, 44 may be applied out to the lateral edge of the front and/or back section. However, in the area of the side edges 9a, 9b, 10a, 10b a narrow strip 24a, 24b of surface of the front and/or back section is preferably left uncoated with adhesive material, because it may be desired to avoid adhesive material within the area of the side seam 6a, 6b of the finished absorbent article 1.

The width 60 of the second gap 58 may be in the range of 8-18 centimetres, specifically 10-15 centimetres.

In other words, the width 60 of the second gap 58 of the first and/or back section 3, 4 may be in the range of 130-70%, specifically 120-80%, or more specifically substantially equal with the average width 57 of the core 5 in the region 31, 32 of the first and/or back section 3, 4, respectively.

Still in other word, the width 60 of the second gap 58 of the first and/or back section 3, 4 may be in the range of 30-70%, specifically 35-65%, of the maximal length 71 of each side portion of second adhesive material 43 applied to the first and/or back section 3, 4 respectively.

According to some exemplary embodiments, the area of the second gap 58 excluding the area of the first gap 55 has an adhesive coating weight of 0.1-7 g/m2, specifically 1-4 g/m2. This area corresponds essentially to the area being coated with the first adhesive material 44.

The area on lateral sides of the second gap 58 has an adhesive coating weight of 1.5-20 g/m2, specifically 2-15 g/m2. This area corresponds essentially to the area being coated with both the first and the second adhesive material 43, 44.

30 The second adhesive material 43 is applied with an adhesive coating weight of 2-15 g/m2, specifically 3-12 g/m2.

When the second adhesive material 43 is applied on the elastic threads 17 the resulting adhesive coating weight per square metre is determined by taking the coating weight per metre [g/m] applied on each individual elastic thread 17 and dividing with the displacement length [m] 17L between individual elastic threads 17. If the second gap 58 has a plurality of elastic threads 17 with different displacement lengths 17L between individual elastic threads 17 an average displacement length 17L may be used.

The leg elastics 34 in the back section is applied along the leg edge 27a, 27b of the back section 4, which leg edge 27a, 27b in the disclosed example of FIG. 6 is curved. Hence, the elastic threads 17 of the leg elastics 34 must be guided by a moveable guiding tool during manufacturing, thereby making it complicated to apply the second adhesive material 43 on the elastic thread 17 before sandwiching the elastic thread 17 between the sheets 41, 42 of web material. As an alternative, the second adhesive material 43 be applied to one or both the sheets 41, 42 of web material of the laminated elastic web material. This is illustrated in FIG. 6 for the leg elastics 34. The second adhesive material 43 is here applied along a plurality of strips 61a-61d which extend intermittently in the transverse direction X. The width 62 strips 61a-61d in the longitudinal direction Y may for example be selected such that a plurality of strips, positioned edge-to-edge or partly overlapping, jointly cover all or at least most of the track of the leg elastics 34. In the example shown in FIG. 6 four individual strips of the second adhesive material is applied edge-to-edge for covering the entire leg edge 27a, 27b of the back section 4.

If the front and/or back section 3, 4 also have straight elastic threads 17 oriented in the transverse direction X these threads 17 may still be provided with the second adhesive material on the thread 17 itself, as shown in FIG. 6.

Figure 7:
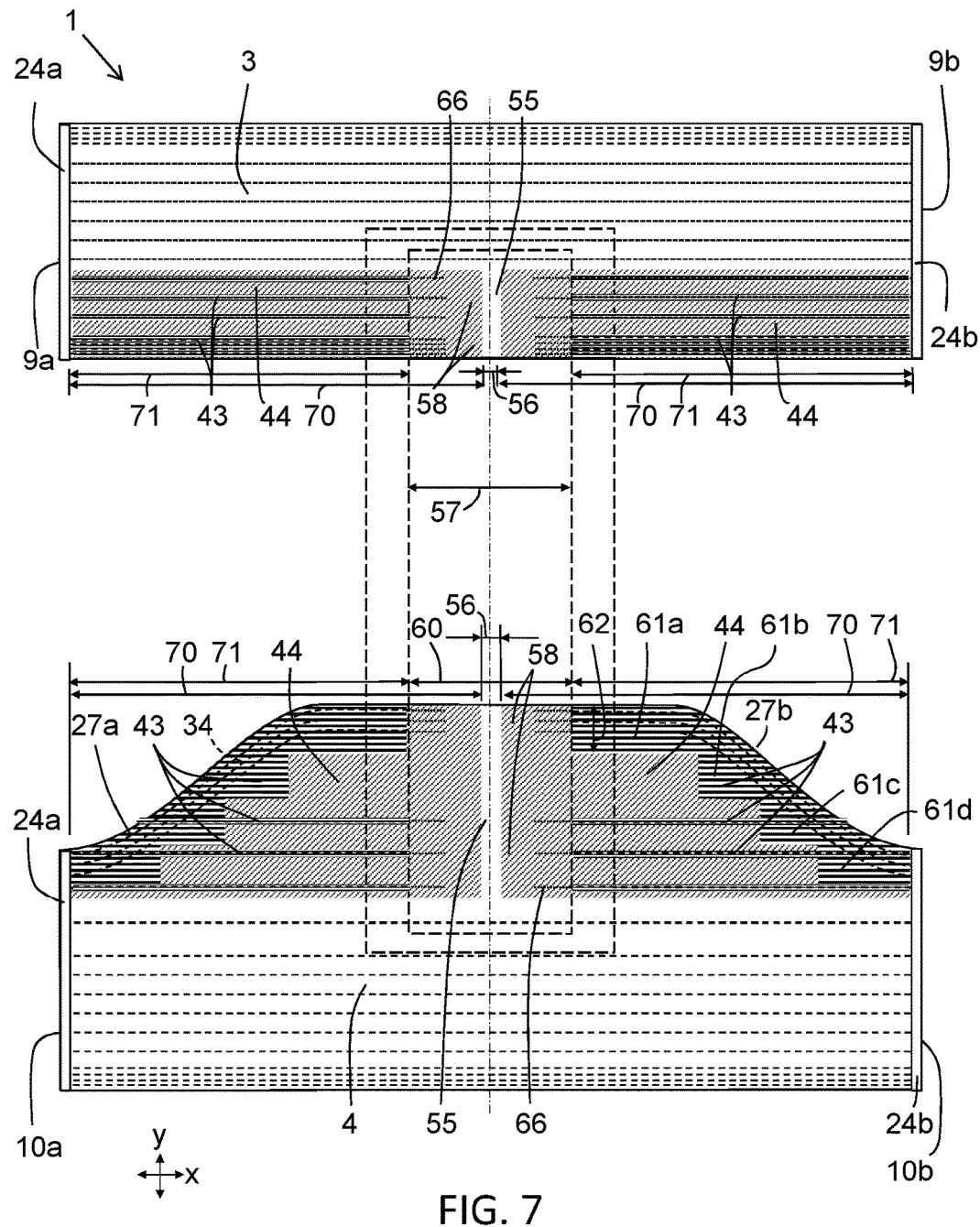
FIG. 7 shows the coating of both the first and second adhesive materials superposed.

FIG. 7 illustrates schematically the flat absorbent article of FIG. 2 where both first and second adhesive material 44, 43 have been applied partly overlappingly in the area marked with hatchings in the front and back sections 3, 4.

As shown in FIG. 7, the first and/or the second gap 56, 58 may have a substantially rectangular shape.

As also shown in FIG. 7, each of the first and second gap 56, 58 may extend over the path of a plurality of interrupted elastic threads 17.

The elastic threads 17 within the second gap 58, but outside of the first gap 56, corresponds to the snapped-back un-stretched elastic portions 66 of the threads 17. These un-stretched elastic portions 66 of the threads 17 are deactivated due to the lack of second adhesive material 43 within the second gap 58, in combination with having the elastic threads 17 interrupted within the second gap 58. Thereby, a controlled snap-back of the ends of the interrupted elastic threads 17 is accomplished, which enables reduced risk for elastic threads 17 delaminating from the laminated web material in the region where the second adhesive material 43 is applied, as well as improved visual appearance due to the straight and parallel orientation of the deactivated end portions 66 within the second gap 58.

The straight and parallel orientation of the deactivated end portions 66 within the second gap 58 is caused mainly by having the first and second sheets 41, 42 of web material forming straight pockets in the laminated web along the paths of the elastic threads 17 prior to having them interrupted. Said pockets are generated by having the first adhesive material 44 bonding together the first and second sheets 41, 42 in the areas between neighbouring elastic threads 17. Upon severing of the elastic threads 17 within the second gap 58 the end portions 66 will perform a controlled snap-back to an un-stretched state but remain within the pockets formed by the first and second sheets 41, 42 and the first adhesive material 44, such that the snapped-back un-stretched elastic end portions 66 of the threads 17 have a straight and parallel orientation within the second gap 58. As a result, the ends 66 of the interrupted elastic threads 17 do not merely arbitrarily hang around in an un-controlled fashion.

Obviously, some of the snapped-back un-stretched elastic end portions 66 of the elastic threads 17 may have a low level of bonding to at least one sheets 41, 42 of web material of the laminated web within the pocket by means of first adhesive material 44 after the interrupting operation, but some of the snapped-back un-stretched elastic end portions 66 of the threads 17 may also be entirely loose within the respective pocket.

By selecting the width 56 of the first gap 55 in the transverse direction X to be smaller than the width 60 of the second gap 58 in the transverse direction X, an adhesive gradient is provided in the region 31, 32 as seen from a centre of the absorbent article 1 towards the lateral edges of the absorbent article 1. Depending on where the first and second adhesive material 44, 43 is applied in the region 31,32 the adhesive gradient may not be present within the entire region 31, 32, but only along certain straight or curved lines, in particular along those lines which the interrupted elastic threads 17 extend.

The adhesive gradient has several advantages. For example, the omission of both the first and second adhesive material 44, 43 in the first gap 55 enables a thread 17 interrupting tool to engage the absorbent article 1 without contacting the first or second adhesive material 43, 44. Thereby the risk for soling the interrupting tool with adhesive material 44, 43 is reduced, thereby reducing the need for maintenance of the manufacturing equipment. However, for the purpose of avoiding having a potentially negative aesthetical appearance caused by pocket-effect in the area of the first gap 55. i.e. having the sheets 41, 42 of web material delaminating and being loose from each other in the first gap 55, the width 56 of the first gap 55 is preferably held relatively small, in the transverse direction X. The lower limit of the width 56 of the first gap 55 is partly set by the width of the interrupting tool, but mainly for allowing certain variation in manufacturing tolerances.

The width 60 of the second gap 58 controls the width of the flat-front and/or flat-back area. The first adhesive material 44 is not strong enough for enabling the elastic threads 17 within the region to generate any gathering effect within the second gap 58. Consequently, the interrupted elastic threads 17 may be deemed inactivated in the second gap 58 upon interrupting the elastic threads 17, thereby generating the desired flat front and/or flat back design.

Figure 8:
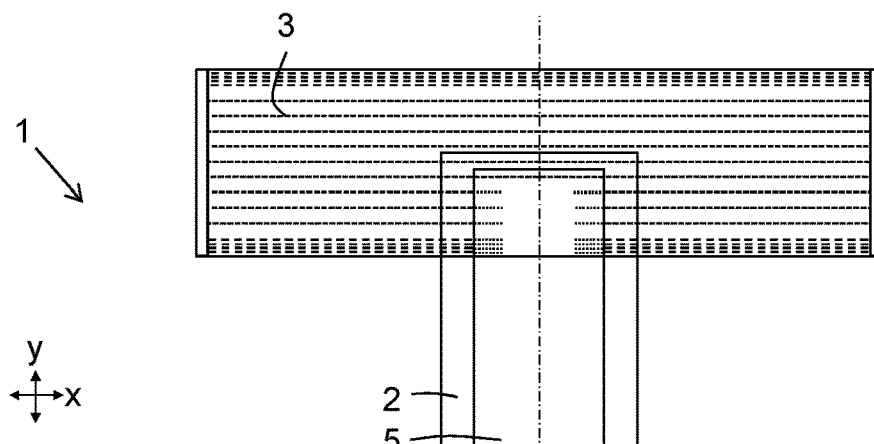
FIG. 8 shows an alternative embodiment where both the front and back sections have rectangular shape.

FIG. 8 illustrates schematically a further exemplary embodiment of the disclosure, in which the back section 4 has been shaped into a rectangular shape, which here has a substantially identical shape as the front section 3. Many further alternative shapes of the front and back sections 3, 4 are possible.

Figure 9:
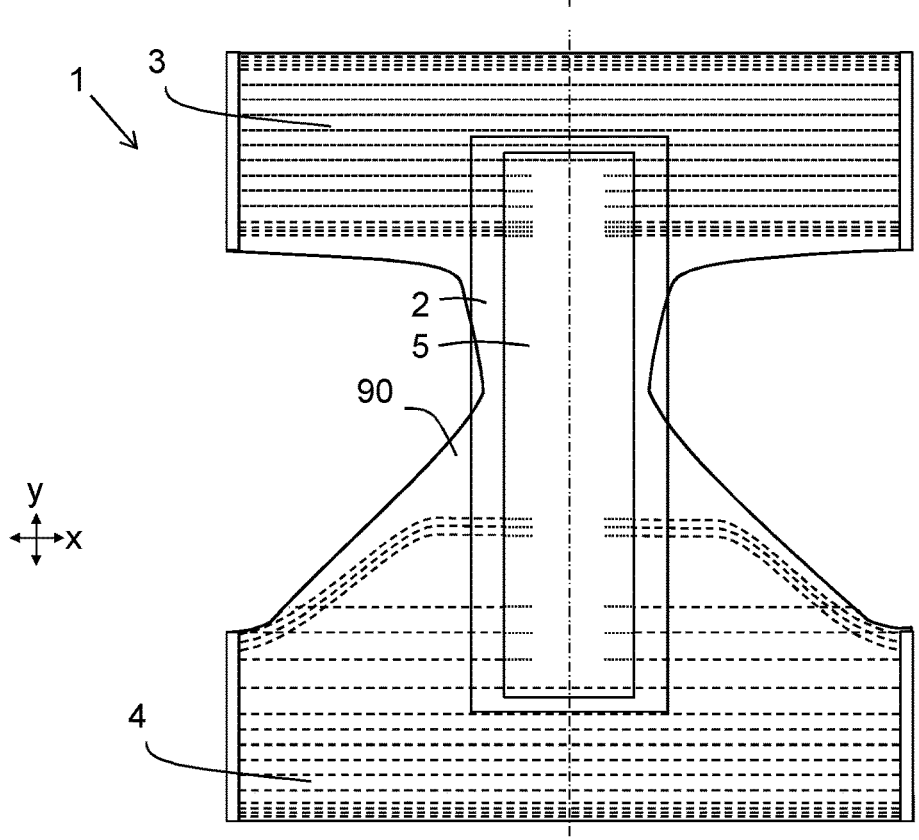
FIG. 9 shows an alternative embodiment where chassis having front section, back section and crotch section is made of a single piece.

Finally, FIG. 9 shows schematically a pant-type diaper in a flat state where the chassis is made of a single piece having a front section 3, a back section 4 and a crotch section 90, wherein all said sections are made of a single piece of material.

The method for manufacturing the absorbent article has been disclosed above. In detail, it comprises the steps of:

forming a chassis from a laminated web material and having a front section 3 and a back section 4, wherein a region of the front and/or back section 3, 4 is made of a laminated elastic web material comprising a plurality of elastic threads 17 extending from a location adjacent a first lateral side of the front and/or back section to a location adjacent an opposite lateral side of the front and/or back section 3, 4, wherein a first adhesive material 44 primarily for securing sheets 41, 42 of web material of the laminated web material to each other is applied from a location adjacent a first lateral side of the region 31, 32 to a location adjacent an opposite lateral side of the region 31, 32, while leaving a first gap 55 in a central area of the absorbent article 1 free from the first adhesive material 44, wherein a second adhesive material 43 primarily for securing the elastic threads 17 to the sheets 41, 42 of laminated web material is applied from a location adjacent a first lateral side of the region 31, 32 to a location adjacent an opposite lateral side of the region 31, 32, while leaving a second gap 58 in a central area of the absorbent article 1 free from the second adhesive material 43, wherein a width 56 of the first gap 55 in the transverse direction X is smaller than a width 60 of the second gap 58 in the transverse direction X, such that an adhesive gradient is provided in the region 31, 32 as seen from a centre of the absorbent article 1 towards the lateral edges of the absorbent article 1, locating an absorbent insert 2 having an absorbent core 5 mainly in a crotch portion of the absorbent article 1 and connecting the absorbent insert 2 to the front and back sections 3, 4, cutting said elastic threads 17 within the area of first gap 55, and attaching side edges 9*a*, 9*b* of the front section 3 to side edges 10*a*, 10*b* of the back section 4 along side seams 6*a*, 6*b*.

The term "extended state of the absorbent article" is herein defined as a state in which the absorbent article 1 has been extended in all four direction to such an extent that all the elastic threads 17 contained therein are extended to such an extent that they no longer gather any part of the product, but the entire absorbent article is completely flat and in an un-gathered state. The article is extended only to such an extent that this flat condition is reached.

The term "active elastic thread" refers to piece of elastic web material that includes an elastic thread that has been has been attached to said piece of elastic web material in a tensioned state, such that the piece of elastic web material gathers upon releasing the tensioning of the elastic thread. A piece of web material having an active elastic thread is elasticised, whereas a piece of elastic web material lacking an active elastic thread, e.g. maybe including a passive elastic thread, is not elasticised.

By "absorbent article" is meant an article that absorbs or is adapted to absorb bodily fluids, such as urine and/or blood.

The nonwoven material layers or webs of the present disclosure forming the front and back sections may for example be selected from, for example, of spunbond, air laid, wet laid, carded, electro spunned or meltblown nonwovens. The nonwoven material may be bonded by multiple techniques, e.g. by needling, hydroentangling, or heat bonding.

The nonwoven material of the disclosed products is a mixture of natural and synthetic materials. Natural fibres are for instance cellulosic fibres or fibres from regenerated cellulose.

The term "elastic thread" is intended to mean an elastic strand or elastic thread which is made of elastic material, such as e.g. natural or synthetic rubber, thermoplastic elastomers, such as thermoplastic polyurethane or styrene block co-polymers or elastane, also referred as to spandex (polyurethane-polyurea copolymer). The threads 17 may be of the elastane type that is available under the trade name "LYCRA", but any suitable elastic thread may be used. The threads 17 may have a linear mass density, dtex, of about 80-1200 dtex.

The elastic threads 17 are elongated during the production process from about 50 to about 300% of the initial, non-tensioned original length, more preferably 100-250% and most preferably 150-220% of the initial, non-tensioned original length. The elastic threads 17 should preferably be of a type that are able to tolerate an elongation of at least about 200% without breaking, so that they can be safely used in the production process without risk for breaking.

Further information with respect to material about the elastic web material is disclosed in WO2014098683 A1, which is incorporated herein in its entirety.

The absorbent core may comprise any conventional material suitable for absorbing discharged bodily wastes, such as cellulosic fluff pulp, tissue layers, highly absorbent polymers (superabsorbents), absorbent foam materials including hydrogel-foam material, absorbent nonwoven materials or the like.

The absorbent core may have a liquid permeable topsheet placed on the side intended to face the skin of a user, and a liquid impermeable backsheet placed on the side of the absorbent body intended to face the garment of a user. Generally, the liquid permeable topsheet comprises or consist of a nonwoven material. The topsheet material may further be composed of tow fibres, porous foams, apertured plastic films etc. As mentioned above, the materials suited as topsheet materials should be soft and non-irritating to the skin and be readily penetrated by body fluid, e.g. urine or menstrual fluid, and display low rewetting properties.

The liquid impermeable backsheet may consist of a thin plastic film, e. g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent body, while still preventing liquids from passing through the backsheet material.

The topsheet and backsheet may be connected to each other for example by adhesive bonding, gluing or welding by heat or ultrasonic. The topsheet and/or the backsheet may further be attached to the absorbent body by any method known in the art, such as adhesive, heat-bonding etc.

The topsheet and backsheet of the absorbent core 5 may extend outwardly beyond the area of the absorbent core, thereby defining an absorbent insert 2 comprising an absorbent core 5.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive. It should be understood that the present absorbent articles and its components and methods are not intended to be limited to the particular forms disclosed. Rather, they are intended to include all modifications, equivalents, and alternatives falling within the scope of the claims. They are further intended to include embodiments that may be formed by combining features from the disclosed embodiments, and variants thereof.

The invention claimed is:

1. A disposable pant-type absorbent article having a longitudinal direction and a transverse direction, said disposable pant-type absorbent article comprises:
    a chassis made of laminated web material and having a front section and a back section,
    an absorbent insert located mainly in a crotch portion of the absorbent article and connected to the front and back sections and having an absorbent core,
    wherein a region of the front or back section is made of a laminated elastic web material comprising a plurality of elastic threads extending from a location adjacent a first lateral side of the front or back section to a location adjacent an opposite lateral side of the front or back section, wherein said elastic threads are interrupted in a central area of the absorbent article,
    wherein a first adhesive material primarily for securing sheets of web material of the laminated web material to each other is applied in the region from a location adjacent a first lateral side of the front or back section to a location adjacent an opposite lateral side of the front or back section, while leaving a first gap in the central area of the absorbent article free from the first adhesive material,
    wherein a second adhesive material primarily for securing the elastic threads to the sheets of laminated web material is applied in the region from a location adjacent a first lateral side of the front or back section to a location adjacent an opposite lateral side of the front or back section, while leaving a second gap in the central area of the absorbent article free from the second adhesive material, and
    wherein a width of the first gap in the transverse direction is smaller than a width of the second gap in the transverse direction, such that an adhesive gradient is provided in the region as seen from a centre of the absorbent article towards the lateral edges of the absorbent article.

2. The disposable pant-type absorbent article according to claim 1, wherein the width of the first gap is in the range of 1-7 centimetres.

3. The disposable pant-type absorbent article according to claim 1, wherein the width of the first gap is in the range of 5-50% of the average width of the core in the region.

4. The disposable pant-type absorbent article according to claim 1, wherein the width of the second gap is in the range of 8-18 centimetres.

5. The disposable pant-type absorbent article according to claim 1, wherein the width of the second gap is in the range of 130-70% of the average width of the core in the region.

6. The disposable pant-type absorbent article according to claim 1, wherein the first adhesive material is applied with a coating weight of 0.1-7 g/m² in the area of the second gap excluding the area of the first gap.

7. The disposable pant-type absorbent article according to claim 1, wherein the second adhesive material in the area on lateral sides of the region outside the second gap has an adhesive coating weight of 1.5-20 g/m².

8. The disposable pant-type absorbent article according to claim 1, wherein the first adhesive material is applied with an adhesive coating weight of 0.1-7 g/m².

9. The disposable pant-type absorbent article according to claim 1, wherein the second adhesive material is applied with an adhesive coating weight of 2-15 g/m².

10. The disposable pant-type absorbent article according to claim 1, wherein the second adhesive material is applied with a larger adhesive coating weight per square metre than the first adhesive material.

11. The disposable pant-type absorbent article according to claim 1, wherein the first adhesive material is applied on at least one sheet of web material of the laminated web material.

12. The disposable pant-type absorbent article according to claim 1, wherein the first adhesive material is applied in form of a single coating covering substantially all area within the region except for the area of the first gap, or in a form of a plurality of parallel strips.

13. The disposable pant-type absorbent article according to claim 1, wherein the second adhesive material is applied on the elastic threads of the region prior to being included into the laminated elastic web material.

14. The disposable pant-type absorbent article according to claim 1, wherein the second adhesive material is applied on at least one sheet of web material of the laminated web material.

15. The disposable pant-type absorbent article according to claim 1, wherein the second adhesive material is applied on at least one sheet of web material of the laminated web material along the course of those elastic threads having an orientation diverging from the transverse direction.

16. The disposable pant-type absorbent article according to claim 1, wherein each of the first and second gaps (55, 58) extends over a plurality of elastic threads.

17. The disposable pant-type absorbent article according to claim 1, wherein the first or the second gap have a substantially rectangular shape.

18. The disposable pant-type absorbent article according to claim 1, wherein snapped-back elastic portions of the elastic threads within the second gap are held in straight and parallel configuration by the first adhesive material.

19. A method for manufacturing a disposable pant-type absorbent article having a longitudinal direction and a transverse direction, in a continuous process, said method comprises:

forming a chassis from a laminated web material and having a front section and a back section, wherein a region of the front or back section is made of a laminated elastic web material comprising a plurality of elastic threads extending from a location adjacent a first lateral side of the front or back section to a location adjacent an opposite lateral side of the front or back section, wherein a first adhesive material primarily for securing sheets of web material of the laminated web material to each other is applied in the region from a location adjacent a first lateral side of the front or back section to a location adjacent an opposite lateral side of the front or back section, while leaving a first gap in a central area of the absorbent article free from the first adhesive material, wherein a second adhesive material primarily for securing the elastic threads to the sheets of laminated web material is applied in the region from a location adjacent a first lateral side of the front or back section to a location adjacent an opposite lateral side of the front or back section, while leaving a second gap in a central area of the absorbent article free from the second adhesive material, wherein a width of the first gap in the transverse direction is smaller than a width of the second gap in the transverse direction, such that an adhesive gradient is provided in the region as seen from a centre of the absorbent article towards the lateral edges of the absorbent article, locating an absorbent insert having an absorbent core mainly in a crotch portion of the absorbent article and connecting the absorbent insert to the front and back sections, cutting said elastic threads within the area of first gap, and attaching side edges of the front section to side edges of the back section along side seams.

* * * * *